United States Patent [19]

Nakamura et al.

[11] Patent Number: 5,763,182
[45] Date of Patent: Jun. 9, 1998

[54] RPDL PROTEIN AND DNA ENCODING THE SAME

[75] Inventors: Yusuke Nakamura; Yoichi Furukawa, both of Kanagawa, Japan

[73] Assignees: Cancer Institute; Eisai Co., Ltd., both of Tokyo, Japan

[21] Appl. No.: 717,365

[22] Filed: Sep. 23, 1996

Related U.S. Application Data

[62] Division of Ser. No. 528,255, Sep. 14, 1995, Pat. No. 5,659,016.

[30] Foreign Application Priority Data

Sep. 22, 1994 [JP] Japan .................... 6-227876

[51] Int. Cl.⁶ .................... C12Q 1/68; C12N 15/12; C07H 21/04
[52] U.S. Cl. .................... 435/6; 435/172.1; 536/23.1; 536/24.31; 536/24.33
[58] Field of Search .................... 435/6, 69.1, 91.4, 435/172.1, 320.1; 530/350; 536/23.1, 24.3, 24.33

[56] References Cited

PUBLICATIONS

Vidal and Gaber. RPD3 encondes a second facotr required to achieve maximum positive and negative transcriptional states in Saccharomyces cerevisiae. Mol. Cell. Biol. vol. 11(12):6317–6327, Dec. 1991.

Kijima et al., Trapoxin, an antitumor cyclic tetrapeptide, is an irreversible inhibitor of mammalian histone deacetylase. J. Biol. Chem. vol. 268(30):22429–22435, Oct. 25, 1993.

Strebhardt et al. Additional member of the protein–tyrosine kinase family: The src– and lck–related protooncogene c–tkl. PNAS (USA) vol. 84:8778–8782, Dec. 1987.

Marshall. Gene therapy's growing pains. Science. vol. 269:1050–1055, Aug. 25, 1995.

*Primary Examiner*—Nancy Degen
*Assistant Examiner*—William Sandals
*Attorney, Agent, or Firm*—Flynn, Thiel, Boutell & Tanis, P.C.

[57] ABSTRACT

The 5'-terminal partial nucleotide sequence of each clone of a human fetal lung tissue CDNA library was determined. A clone having a novel sequence including a sequence homologous to that of the transcriptional control protein of a yeast was selected from among the above clones and its whole nucleotide structure was determined. It was confirmed that the protein encoded by the gene of the clone was a novel human transcriptional control protein (RPDL protein). Further, an expression vector for expressing the protein and a transformant obtained by transforming with such an expression vector can also be prepared.

27 Claims, No Drawings

RPDL PROTEIN AND DNA ENCODING THE SAME

This is a division of Ser. No. 08/528,255, filed Sep. 14, 1995 now U.S. Pat. No. 5,659,016.

BACKGROUND OF THE INVENTION

1. Field of the Invention

The present invention relates to an RPDL protein which is a novel transcriptional control protein, a process for producing this protein, a method of using the same, a DNA encoding the protein, and a gene analysis method using the DNA. The present invention finds-applications in the pharmaceutical field.

2. Description of the Related Art

Many genes execute selective expression, for example, at a specific time or site or when a certain stimulus has been given. The expression of the genes involves two important steps consisting of producing a mRNA on the basis of information stored in the DNA sequence (transcription) and producing a protein by the action of the mRNA (translation).

It is becoming apparent in recent years that the transcription of genes in eukaryotic cells is skillfully controlled by a plurality of proteins known as transcriptional control proteins.

Analyzing in detail the mechanism of the above transcriptional control is a task extremely important from the viewpoint of learning the selective expression control mechanism of genes, namely, the cell differentiation or amplification or various gene activities and ultimately the fundamental system relating to, for example, life and death. It is expected that the analysis of the mechanism of the above transcriptional control would break through difficult problems of not only tumors but also other various diseases and abnormalities, and further, aging, dementia, obesity, etc.

For the elucidation of the transcriptional control mechanism, it is essential to achieve "understanding the material bases of associated factors (transcriptional control protein, etc.)", "understanding the interaction between such factors", "understanding the whole process through a plurality of interactions", and "working out a systematic understanding through commonality and diversity" [see Masami Horikoshi et al, Tanpaku-shitsu•Kakusan•Koso (Protein, Nucleic Acid and Enzyme), Vol.38, No.5, p.p.831–841 (1993)].

Studies on structural fundamentals such that some basic transcription factors recognize specific sequences of the DNA and bind therewith have been advanced with the use of viruses, bacteria, yeasts, and the like. However, for example, the number of constituent factor groups is so large that elucidation is still being awaited in various fields such as the interaction between factors, the interaction of the factor with a component of transcription initiation complex, such as RNA polymerase, and the commonality in the control mechanism between viruses, bacteria, yeasts and human. Therefore, a marked progress of the analysis described above based on the recent gene isolations, especially, the cDNA clonings of factors associated with the human transcriptional control mechanism is being expected.

Known transcriptional control proteins include those specific for some genes and those commonly acting on a wide variety of genes. From the viewpoint of function, the known transcriptional control proteins include not only those capable of activating the transcription or inactivating the same but also those having both of the above capabilities [see M. Ptashne, Scientific American, Vol.260, p.p.40–47 (1989)].

Up to now, studies on eukaryotic cells in this field have been conducted with the use of yeast as the model from the practical point of view, and it has been suggested that the fundamental mechanism thereof applies to human cells as well. The transcriptional control protein not only commonly acting on many genes but also having both the functions of activation and inactivation is considered as being especially important and, therefore, it is apparent that the studies on the effects exerted by its mutation with the use of yeast only have reached a limit.

Accordingly, isolating a human gene encoding the above important transcriptional control protein and identifying the protein has an extremely important significance in that a marked progress can be realized in the direct elucidation of the transcriptional control mechanism of the cells of multicellular organisms having such aspects as development, differentiation and tissue, especially, human per se.

DISCLOSURE OF THE INVENTION

SUMMARY OF THE INVENTION

An object of the present invention is to provide an important human transcriptional control protein not only commonly acting on many target genes but also having both the functions of activation and inactivation, and a gene encoding the protein. Another object of the present invention is to provide a gene analysis method useful for elucidative studies on the mechanism of control of human gene transcription and on the effects on human cells caused by the mutation of the gene encoding the human transcriptional control protein with the use of the transcriptional control protein and DNA encoding the same.

The yeast transcription factor RPD3 controls not only the transcription of high- and low-affinity potassium transporter gene TRK2 but also the transcription of many genes including genes PHO5, STE6 and TY2 as the target. Further, it is known that the yeast PRD3 protein has both the functions of activation and inactivation [see M. Vidal and R. F. Gaber, Mol. Cel. Biol. Vol.11, p.p.6317–6327 (1991)].

The present inventors have determined the 5'-terminal nucleotide sequence of each clone derived from a cDNA library prepared from human fetal lung and have found a clone exhibiting homology with the sequence of the RPD3 gene of a yeast. Further, they have determined the DNA sequence of this clone and have obtained a full-length cDNA encoding a novel protein. It has been confirmed that the amino acid sequence of the protein encoded by this cDNA exhibits a significant similarity to that of the yeast RPD3 and this protein is a novel human transcriptional control protein that has never been reported.

Moreover, the present inventors have confirmed that the gene encoding this protein is an important gene which is expressed in all the studied human tissues, excluding the brain, by a gene analysis according to the Northern blotting technique using the above cDNA as a probe.

Furthermore, the present inventors have confirmed that the gene encoding this protein is localized at 1p34.1 on the short arm of chromosome 1, the region where a deletion is recognized in mammary and gastric carcinomas, by chromosomal mapping according to the FISH (fluorescent in situ hybridization) technique using the above cDNA as a probe.

The present invention has enabled not only the production of a transformant having, introduced thereinto, the cDNA encoding the above human transcriptional control protein or a DNA obtained by artificially mutating the same by introducing the cDNA or the DNA into a host such as *E. coli*, yeast, an insect cell and a mammal cell, but also the production of the above protein or its variant with the use of the transformant and, further, the production of an antibody capable of binding with the above protein or its variant. Moreover, the present invention has enabled, on the level of human cells, not only the analyses of the interaction between the above protein and other factors capable of binding therewith, human genes controlled as the target and the activation and inactivation functions of the above protein as the transcriptional control factor, but also studies of the effects caused by the mutation of the DNA encoding the above protein.

Thus, the present invention provides an RPDL protein having an amino acid sequence, comprising the whole or a part of the amino acid sequence specified in SEQ ID NO:1, or a variant of said RPDL protein. In the above explanation, "the variant of said RPDL protein" is an RPDL protein having an amino acid sequence comprising the whole or a part of an amino acid sequence which is identical with the one specified in SEQ ID NO:1 except that one or more amino acids are added thereto, deleted therefrom or inserted thereinto, or that one or more amino acids are substituted for one or more amino acids contained in SEQ ID NO:1, and acts in the same manner as that of said RPDL protein having an amino acid sequence comprising the whole or a part of the amino acid sequence specified in SEQ ID NO:2.

Further, the present invention provides a DNA encoding said RPDL protein or a variant of said RPDL protein; a vector which contains a DNA encoding said RPDL protein or a variant of said RPDL protein; a transformant having, introduced thereinto, said vector; a process for producing said RPDL protein or a variant of said RPDL protein, which comprises culturing said transformant and recovering an expression product thereof; and a polyclonal antibody or a monoclonal antibody capable of combining with said RPDL protein or a variant of said RPDL protein.

Furthermore, the present invention provides a DNA probe having a DNA sequence, said DNA sequence comprising the whole or a part of the DNA sequence specified in SEQ ID NO:2 or comprising a sequence complementary to the whole or a part of the DNA sequence specified in SEQ ID NO:2; a DNA primer having a DNA sequence, said DNA sequence comprising a part of the DNA sequence specified in SEQ ID NO:2 or comprising a sequence complementary to a part of the DNA sequence specified in SEQ ID NO:2; and a gene analysis method for an RPDL protein characterized by hybridizing said DNA probe or said DNA primer with a subject DNA.

In other words, the present invention relates to (1) a protein comprising the whole or a part of the protein represented by SEQ ID NO:1 or a variant thereof; (2) a DNA comprising the whole or a part of the DNA represented by SEQ ID NO:2 or a mutant thereof, (3) a plasmid including the above DNA and a transformant carrying the same, (4) a process for producing the above protein, (5) an antibody capable of binding with the above protein, and (6) a probe or primer including a part of the above DNA sequence and a gene analysis method or gene amplification method characterized by using the same.

The present invention will be described in detail below.

DETAILED DESCRIPTION OF THE INVENTION (1) Isolation of cDNA clone and confirmation of nucleotide sequence and amino acid sequence cDNA was synthesized on the basis of mRNA derived from human fetal lung tissue and a cDNA library containing cloned cDNA inserts in a given direction was prepared. The nucleotide sequence of each clone of this library was determined partially from the 5'-terminal side and one clone having a nucleotide sequence homologous with the RPD3 gene of a yeast was obtained. Further, the whole nucleotide sequence of this clone was determined with the result that the desired full-length cDNA sequence was obtained.

The cDNA obtained by the above procedure was confirmed as having a novel DNA sequence represented by SEQ ID NO:2 and the amino acid sequence of a novel protein encoded thereby was deduced as shown in SEQ ID NO:1. The present inventors designated the protein having the SEQ specified in SEQ ID NO:1 as a RPDL protein, this designation being employed throughout this description.

The DNA of the present invention and a DNA complementary to said DNA can find applications in gene and gene expression analyses by the use of a part thereof as a primer or probe. The term "a part of the DNA" as used herein means a continuous sequence of at least six nucleotides, preferably at least eight nucleotides, still more preferably, at least ten nucleotides, and most preferably, 10 to 12 nucleotides or 15 to 25 nucleotides corresponding to (i.e., contained in or complementary to) the nucleotide sequence of the DNA according to the present invention. The primer or probe of the present invention which is an oligonucleotide or polynucleotide may contain also at least one nucleotide(s) not corresponding to the nucleotide sequence of the DNA encoding the RPDL protein.

The protein of the present invention can find applications in antibody preparation and agents for study and diagnostics containing such antibodies by the use of the whole or a part thereof as an epitope. The term "epitope" means an antigenic determinant of a polypeptide. It is well known that the epitope is generally composed of at least 5 amino acid residues and that a polypeptide composed of 6 amino acid residues combines with an antibody [see WO of PCT Patent Applications No. 8403564, published on Sep. 13, 1984 (Assignee: COMMONWEALTH SERUM LABS AND GEYSEN, H. M.)]. The term "a part of the protein" as used herein refers to a polypeptide comprising at least about 3 to 5 consecutive amino acid residues, preferably at least about 8 to 10 consecutive amino acid residues, and still more preferably, at least about 11 to 20 consecutive amino acid residues, on the basis of the amino acid sequence of the protein of the present invention. Needless to say, use can be made of even a polypeptide comprising at least about 20 amino acid residues. The polypeptide described above may contain also at least one amino acid residues not corresponding to the amino acid sequence of the RPDL protein.

The present invention comprehends RPDL proteins which are substantially equivalent to the RPDL protein having an amino acid SEQ specified in SEQ ID NO:1 and which are obtained by addition, deletion, insertion or substitution of one or more constituent amino acid residues of the above protein. Such equivalents are included in the present invention as long as they exert similar effects in the study and diagnosis regarding the RPDL protein. As in the protein above, DNAs which are substantially equivalent to the DNA encoding the RPDL protein having an amino acid sequence specified in SEQ ID NO:1 and which are obtained by addition, deletion, insertion or substitution of one or more constituent nucleotides of the above DNA, i.e., equivalents, are also included in the present invention.

(2) Recombinant expression vector and preparation of transformant and protein

A transformant can be obtained by inserting the DNA of the present invention or a part thereof into a suitable vector and transfecting this vector into suitable host cells. Human RPDL protein or a part thereof can be produced in a large quantity by culturing the transformant in the customary manner and separating it from the resultant culture. More particularly, a recombinant expression vector can be prepared by relegating the above DNA or a fragment thereof to a vector suitable for the expression downstream of the promoter according to the customary procedure in which a restriction enzyme and DNA ligase are employed. Examples of suitable vectors include plasmids pBR322 and pUC18 derived from *Escherichia coli*, plasmid pUB110 derived from *Bacillus subtilis*, plasmid pRB15 derived from yeast, bacteriophage vectors λgt10 and λgt11, and vector SV40. The vectors are not particularly limited as long as they can be replicated or amplified in the host. The promoter and terminator are also not particularly limited as long as they suit the host employed in the expression of the DNA sequence. Appropriate members thereof can be used in combination in accordance with the host. The DNA to be employed is not limited to the one having the DNA sequence specified in SEQ ID NO:2. Use may be made of a DNA having a DNA sequence resulting from intentional or unintentional substitution, deletion, insertion and/or addition conducted individually or in combination at a part of the DNA sequence of SEQ ID NO:2. Further, use may be made of one chemically synthesized.

The obtained recombinant expression vector is introduced into a host in accordance with any of the competent cell method [see J. Mol. Biol., Vol.53, p.154 (1970)], the protoplast method [see Proc. Natl. Acad. Sci. USA, Vol.75, p.1929 (1978)], the calcium phosphate method [see Science, Vol.221, p.551 (1983)], the in vitro packaging method [see Proc. Natl. Acad. Sci. USA, Vol.72, p.581 (1975)], the virus vector method [see Cell, Vol.37, p.1053 (1984)], etc., thereby preparing a transformant. Any of *Escherichia coli*, *Bacillus subtilis*, yeast, insect cells, animal cells and the like is used as the host. The obtained transformant is cultured in a medium suitable for the host. The culturing is generally conducted at 20° to 45° C. and at pH of 5 to 8, in which aeration and agitation are executed according to necessity. The separation of the RPDL protein from the resultant culture and its purification may be conducted by an appropriate combination of conventional separation and purification methods. Examples of these conventional methods include salting out, solvent precipitation, dialysis, gel filtration, electrophoresis, ion exchange chromatography, affinity chromatography, and reversed-phase high-performance liquid chromatography.

(3) Preparation of antibody

Antibodies can be prepared by the conventional method in which the whole or a part of the RPDL protein is used as an antigen. For example, a polyclonal antibody can be prepared by giving a plurality of subcutaneous, intramuscular, intraperitoneal or intravenous inoculations of the antigen to an animal such as a mouse, a guinea-pig and a rabbit to thereby satisfactorily immunize the same, collecting the blood specimen from the animal, and performing serum separation. In this procedure, commercially available adjuvants can be used.

A monoclonal antibody can be prepared by, for example, conducting the fusion of splenocytes of a mouse immunized with the RPDL protein with commercially available mouse myeloma cells to thereby prepare a hybridoma and either culturing the hybridoma followed by separation of the antibody from the resultant supernatant or administering the hybridoma to a mouse followed by separation of the antibody from the mouse ascites.

The RPDL protein as an antigen does not necessarily have to possess the whole amino acid structure and use may be made of a peptide having a partial structure of the protein, a variant or derivative of the protein, or a fusion peptide resulting from the fusion with another peptide. The method for preparing these is not critical and it may be biological or chemosynthetic.

The obtained antibody enables the identification and quantity determination of RPDL protein in human biospecimens and can be used in, for example, various agents.

The immunoassay of RPDL protein may be conducted in accordance with the generally known procedure and can be executed by, for example, any of the fluorescent antibody technique, passive agglutination and enzyme antibody technique.

(4) Analyses of mutation and abnormality of gene

Any mutation of a gene encoding the RPDL protein can be analyzed by the use of a probe comprising a restriction enzyme fragment of the DNA provided by the present invention or by the use of, as a primer, an oligonucleotide obtained by appropriately selecting a suitably positioned nucleotide sequence from the DNA and synthesizing therewith.

Also, any abnormality such as insertion and deletion in the gene of a specimen can be detected by the above analysis.

The *Escherichia coli* L1-3977 carrying the plasmid containing the DNA encoding the above RPDL protein was deposited with National Institute of Bioscience and Human-Technology, Agency of Industrial Science and Technology, Ministry of International Trade and Industry under the accession number FERM BP-4805 on Sep. 21, 1994.

The use of a substance including the whole or a part of each of the human RPDL protein and the DNA encoding the protein according to the present invention has enabled analyses on the level of human cells not only of the functions of the above protein as a transcriptional control factor and the gene per se but also of the effects of any variation of the above protein. It is apparent that the protein of the present invention is an important transcriptional control protein commonly acting on many target genes and having both functions of activation and inactivation from the viewpoint of the homology of its amino acid sequence with that of the yeast RPD3. The contribution of the above investigations to the elucidation of the fundamental working of human cells, such as differentiation, amplification, activity and life and death thereof, is being anticipated. Moreover, the sequence structure of the above gene and its location on the chromosome have been defined, so that it can be anticipated that its relationships with not only tumors but also other various diseases and abnormalities of the gene are elucidated and its application is found in the pharmaceutical field.

EXAMPLES

The present invention will be concretely described in detail with reference to the following Examples which in no way limit the scope of the invention.

Example 1 Preparation of human fetal lung cDNA library cDNA was synthesized on the basis of mRNA derived from human fetal lung tissue (purchased from Clontech) and a cDNA library containing cloned cDNA inserts in a given direction was prepared by the use of UniZAPxR vector kit (purchased from Stratagene).

Example 2 Selection of clone

The nucleotide sequence of each of 2058 clones of the cDNA library prepared in Example 1 was partially determined from the 5'-terminal side. The resultant nucleotide sequences were compared with the known nucleotide sequences of a data base to find out one clone L1-3977 having homology with the yeast RPD3. A partial sequence (256 bp) of the clone L1-3977 exhibited a homology of 60.2% with the RPD3 gene (Accession No. S66438, 1645 bp) of yeast (*Saccharomyces cerevisiae*) in the range of 176 bp.

Example 3 Sequencing of full-length cDNA and characteristics of structure.

The DNA sequence of the clone L1-3977 obtained in Example 2 was determined by the Dideoxy method [see F. Sanger et al., Proc. Natl. Acad. Sci. USA, Vol.74, p.p.5463–5467 (1977)]. As a result, it was found that the clone L1-3977 contained a full-length cDNA having a novel sequence specified in SEQ ID NO:2. The amino acid sequence of a novel protein (sequence ID NO 1, RPDL protein) composed of 482 amino acid residues was deduced from an open reading frame formed of 64th to 1509th nucleotides of the above DNA sequence.

This amino acid sequence exhibited a homology of 60.0% with the RPD3 protein (Accession No. S22284 & P32561, 433 amino acid residues) of yeast (*S. cerevisiae*) in the range of 422 amino acid residues.

The nucleotide sequence of SEQ ID NO:2 (2111 bp) exhibited a homology of 62.1% with the RPD3 gene (Accession No. S66438, 1645 bp) of yeast (*S. cerevisiae*) in the range of 1168 bp. Further, it exhibited a homology as high as 80.9% with the RPD3 homologue gene (Accession No. X78454, 1040 bp) of *Xenopus laevis* in the range of 1034 bp. A homology as high as 94.8% was recognized in the range of 343 amino acid residues between the protein (343 amino acid residues) encoded by the RPD3 homologue gene (Accession No. X78454, 1040 bp) of *Xenopus laevis* and the RPDL protein of the present invention.

The above homology data demonstrate that the RPDL protein of the present invention is an important human transcriptional control protein having the same functions as those of the RPD3 protein of a yeast. In addition, the nucleotide sequence (2111 bp) of SEQ ID NO:2 has exhibited a homology as high as 78.9% with the nucleotide sequence of the 3'-noncoding region of proto-oncogene c-tkl (chicken tyrosine kinase proto-oncogene) in a range as wide as 1534 bp, so that the importance of the RPDL protein of the present invention in the transcriptional control mechanism has also been supported from the recent information on the association of the gene 3'-noncoding region with the control of transcription and translation.

Example 4 Analysis of expression in various human tissues

Expression analysis by Northern blot system (purchased from Clontech) was conducted with respect to various human tissue mRNAs with the use of the cDNA obtained in Example 3 as a probe. The conditions recommended by the manufacturer were obeyed on hybridization and washing, and autoradiography was conducted at −80° C. for 16 hours. Actin was used as a control. As a result, expression was recognized in the form of a mRNA band having a size of about 2.4 kbp in all the studied tissues (heart, kidney, liver, lung, pancreas, placenta, skeletal muscle, large intestine, peripheral leukocyte, ovary, prostate, small intestine, spleen, testis, and thymus gland) except the brain. While expression scarcely occurred in the brain, relatively strong expression occurred in the heart, pancreas and testis and relatively weak expression in the kidney.

Example 5 Chromosome mapping of the gene

The cDNA obtained in Example 3 was used as a probe for investigating the location of the gene encoding the RPDL protein of the present invention on the chromosome. That is, the location on the chromosome with which the above probe hybridized was determined by the FISH method [see Inazawa et al., Genomics, Vol.10, p.p.1075–1078 (1991)]. As a result, the location was identified as being at lp34.1 on the short arm of chromosome 1. This location was the one at which deletion was recognized in mammary carcinoma [see A. Borg et al., Genes Chromosome Cancer, Vol.5, p.p.311–320 (1992)] and gastric carcinoma [see T. Sano et al., Cancer Res., Vol.51, p.p.2926–2931 (1991)].

Example 6 Construction of recombinant RPDL protein expression vector

A partial sequence including the protein coding region was amplified by PCR with the use of the cDNA obtained in Example 3 as a template. BamHI and EcoRI cleavage sites were added to the 5'-terminus of one primer and the 5'-terminus of the other primer, respectively. The obtained amplification product was digested with BamHI and EcoRI. The resultant fragment was inserted into expression vector pGEX-2T (purchased from Pharmacia) preliminaly digested with BamHI and EcoRI, thereby constructing expression plasmid pGST-RPDL. *E. coli* DH5α was transformed with the plasmid pGST-RPDL and resulting transformants were selected based on ampicillin resistance, thereby obtaining a transformant capable of expressing a fusion protein of glutathione-S-transferase and RPDL protein.

Example 7 Expression of recombinant RPDL protein and its purification

The transformant obtained in Example 6 was cultured, and a recombinant RPDL fusion protein was extracted from the resultant culture and purified.

Specifically, the transformant was cultured by shaking the same in 100 ml of LB medium (1% peptone, 0.5% yeast extract and 1% NaCl) at 37° C. overnight. The resultant liquid culture was diluted tenfold with LB medium preliminarily heated to 37° C. and the resulting dilution was further cultured at 37° C. for 30 to 90 minutes, thereby obtaining a culture of logarithmic growth phase. Isopropyl β-D-thiogalactopyranoside was added to 1 l of the culture so that the final concentration thereof was 1 mM, followed by culturing for 3 to 4 hours. The culture was centrifuged to thereby separate bacterial cells. 10 ml of a column buffer (150 mM NaCl, 16 mM $Na_2HPO_4$, 4 mM $NaH_2PO_4$, pH 7.3) was added to bacterial cells transformed with the expression vector pGST-RPDL, followed by sonication. A soluble fraction of a supernatant resulting from the cell disruption was applied to a glutathione-Sepharose 4B column (purchased from Pharmacia). The column was washed with the column buffer and then elution was conducted with an eluent containing 5 mM reduced glutathione. The eluted fraction was analyzed and fractionated by SDS polyacrylamide electrophoresis. As a result, a fraction in which the desired GST fusion protein of about 80 kDa was detected as a main band was obtained from the transformant constructed with the plasmid pGST-RPDL.

What we claim is:

1. A gene analysis method for an reduced potassium dependency lung (RPDL) protein comprising the step of specifically hybridizing a DNA probe with a subject DNA, wherein said DNA probe has a DNA sequence comprising at least six consecutive nucleotides of the DNA sequence specified in SEQ ID NO:2.

2. The gene analysis method of claim 1, wherein said DNA sequence comprises at least 8 consecutive nucleotides of the DNA sequence specified in SEQ ID NO: 2.

3. The gene analysis method of claim 1, wherein said DNA sequence comprises at least 10 consecutive nucleotides of the DNA sequence specified in SEQ ID NO: 2.

4. The gene analysis method of claim 1, wherein said DNA sequence comprises at least 12 consecutive nucleotides of the DNA sequence specified in SEQ ID NO: 2.

5. The gene analysis method of claim 1, wherein said DNA sequence comprises at least 15 consecutive nucleotides of the DNA sequence specified in SEQ ID NO: 2.

6. The gene analysis method of claim 1, wherein said DNA sequence comprises at least 25 consecutive nucleotides of the DNA sequence specified in SEQ ID NO: 2.

7. The gene analysis method of claim 1, wherein said DNA sequence comprises the DNA sequence specified in SEQ ID NO: 2.

8. A gene analysis method for an reduced potassium dependency lung (RPDL) protein comprising the step of specifically hybridizing a DNA probe with a subject DNA, wherein said DNA probe has a DNA sequence complementary to at least six consecutive nucleotides of the DNA sequence specified in SEQ ID NO:2.

9. The gene analysis method of claim 8, wherein said DNA sequence is complementary to at least 8 consecutive nucleotides of the DNA sequence specified in SEQ ID NO: 2.

10. The gene analysis method of claim 8, wherein said DNA sequence is complementary to at least 10 consecutive nucleotides of the DNA sequence specified in SEQ ID NO: 2.

11. The gene analysis method of claim 8, wherein said DNA sequence is complementary to at least 12 consecutive nucleotides of the DNA sequence specified in SEQ ID NO: 2.

12. The gene analysis method of claim 8, wherein said DNA sequence is complementary to at least 15 consecutive nucleotides of the DNA sequence specified in SEQ ID NO: 2.

13. The gene analysis method of claim 8, wherein said DNA sequence is complementary to at least 25 consecutive nucleotides of the DNA sequence specified in SEQ ID NO: 2.

14. The gene analysis method of claim 8, wherein said DNA sequence is complementary to the DNA sequence specified in SEQ ID NO: 2.

15. A gene analysis method for an reduced potassium dependency lung (RPDL) protein comprising the step of specifically hybridizing a DNA primer with a subject DNA, wherein said DNA primer has a DNA sequence comprising at least six consecutive nucleotides of the DNA sequence specified in SEQ ID NO:2.

16. The gene analysis method of claim 15, wherein said DNA sequence comprises at least 8 consecutive nucleotides of the DNA sequence specified in SEQ ID NO: 2.

17. The gene analysis method of claim 15, wherein said DNA sequence comprises at least 10 consecutive nucleotides of the DNA sequence specified in SEQ ID NO: 2.

18. The gene analysis method of claim 15, wherein said DNA sequence comprises at least 12 consecutive nucleotides of the DNA sequence specified in SEQ ID NO: 2.

19. The gene analysis of claim 15, wherein said DNA sequence comprises at least 15 consecutive nucleotides of the DNA sequence specified in SEQ ID NO: 2.

20. The gene analysis method of claim 15, wherein said DNA sequence comprises at least 25 consecutive nucleotides of the DNA sequence specified in SEQ ID NO: 2.

21. A gene analysis method for an reduced potassium dependency lung (RWDL) protein comprising the step of specifically hybridizing a DNA primer with a subject DNA, wherein said DNA primer has a DNA sequence comprising a sequence complementary to at least six consecutive nucleotides of the DNA sequence specified in SEQ ID NO:2.

22. The gene analysis method of claim 21, wherein said DNA sequence is complementary to at least 8 consecutive nucleotides of the DNA sequence specified in SEQ ID NO: 2.

23. The gene analysis method of claim 21, wherein said DNA sequence is complementary to at least 10 consecutive nucleotides of the DNA sequence specified in SEQ ID NO: 2.

24. The gene analysis method of claim 21, wherein said DNA sequence is complementary to at least 12 consecutive nucleotides of the DNA sequence specified in SEQ ID No: 2.

25. The gene analysis method of claim 21, wherein said DNA sequence is complementary to at least 15 consecutive nucleotides of the DNA sequence specified in SEQ ID NO: 2.

26. The gene analysis method of claim 21, wherein said DNA sequence is complementary to at least 25 consecutive nucleotides of the DNA sequence specified in SEQ ID NO: 2.

27. A DNA encoding an RPDL protein, wherein said DNA comprises the DNA sequence specified in SEQ ID NO: 2.

* * * * *

UNITED STATES PATENT AND TRADEMARK OFFICE
CERTIFICATE OF CORRECTION

PATENT NO. : 5,763,182
DATED : June 9, 1998
INVENTOR(S) : Yusuke NAKAMURA et al

It is certified that error appears in the above-identified patent and that said Letters Patent is hereby corrected as shown below:

Column 17, line 26; change "(RWDL)" to ---(RPDL)---.

Signed and Sealed this

First Day of December, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
    ( A ) LENGTH: 482
    ( B ) TYPE: amino acid
    ( C ) STRANDEDNESS:
    ( D ) TOPOLOGY: linear ( i i ) MOLECULE TYPE: protein ( v i ) ORIGINAL SOURCE:
    ( A ) ORGANISM: Homo sapiens ( v i i ) IMMEDIATE SOURCE:
    ( A ) LIBRARY: human fetal lung cDNA library ( x i ) SEQUENCE DESCRIPTION: SEQ ID NO: 1:

```
Met  Ala  Gln  Thr  Gln  Gly  Thr  Arg  Arg  Lys  Val  Cys  Tyr  Tyr  Tyr  Asp
 1                   5                        10                       15

Gly  Asp  Val  Gly  Asn  Tyr  Tyr  Tyr  Gly  Gln  Gly  His  Pro  Met  Lys  Pro
                20                        25                       30

His  Arg  Ile  Arg  Met  Thr  His  Asn  Leu  Leu  Leu  Asn  Tyr  Gly  Leu  Tyr
                35                        40                       45

Arg  Lys  Met  Glu  Ile  Tyr  Arg  Pro  His  Lys  Ala  Asn  Ala  Glu  Glu  Met
      50                        55                       60

Thr  Lys  Tyr  His  Ser  Asp  Asp  Tyr  Ile  Lys  Phe  Leu  Arg  Ser  Ile  Arg
 65                        70                       75                       80

Pro  Asp  Asn  Met  Ser  Glu  Tyr  Ser  Lys  Gln  Met  Gln  Arg  Phe  Asn  Val
                85                        90                       95

Gly  Glu  Asp  Cys  Pro  Val  Phe  Asp  Gly  Leu  Phe  Glu  Phe  Cys  Gln  Leu
               100                       105                      110

Ser  Thr  Gly  Gly  Ser  Val  Ala  Ser  Ala  Val  Lys  Leu  Asn  Lys  Gln  Gln
               115                       120                      125

Thr  Asp  Ile  Ala  Val  Asn  Trp  Ala  Gly  Gly  Leu  His  His  Ala  Lys  Lys
130                       135                      140

Ser  Glu  Ala  Ser  Gly  Phe  Cys  Tyr  Val  Asn  Asp  Ile  Val  Leu  Ala  Ile
145                       150                      155                      160

Leu  Glu  Leu  Leu  Lys  Tyr  His  Gln  Arg  Val  Leu  Tyr  Ile  Asp  Ile  Asp
               165                       170                      175

Ile  His  His  Gly  Asp  Gly  Val  Glu  Glu  Ala  Phe  Tyr  Thr  Thr  Asp  Arg
               180                       185                      190

Val  Met  Thr  Val  Ser  Phe  His  Lys  Tyr  Gly  Glu  Tyr  Phe  Pro  Gly  Thr
          195                       200                      205

Gly  Asp  Leu  Arg  Asp  Ile  Gly  Ala  Gly  Lys  Gly  Lys  Tyr  Tyr  Ala  Val
          210                       215                      220

Asn  Tyr  Pro  Leu  Arg  Asp  Gly  Ile  Asp  Asp  Glu  Ser  Tyr  Glu  Ala  Ile
225                       230                      235                      240

Phe  Lys  Pro  Val  Met  Ser  Lys  Val  Met  Glu  Met  Phe  Gln  Pro  Ser  Ala
                245                       250                      255

Val  Val  Leu  Gln  Cys  Gly  Ser  Asp  Ser  Leu  Ser  Gly  Asp  Arg  Leu  Gly
               260                       265                      270

Cys  Phe  Asn  Leu  Thr  Ile  Lys  Gly  His  Ala  Lys  Cys  Val  Glu  Phe  Val
               275                       280                      285
```

| | | | | | | | | | | | | | | |
|---|---|---|---|---|---|---|---|---|---|---|---|---|---|---|
|Lys|Ser<br>290|Phe|Asn|Leu|Pro|Met<br>295|Leu|Met|Leu|Gly|Gly<br>300|Gly|Gly|Tyr|Thr|
|Ile<br>305|Arg|Asn|Val|Ala|Arg<br>310|Cys|Arg|Thr|Tyr|Glu<br>315|Thr|Ala|Val|Ala|Leu<br>320|
|Asp|Thr|Glu|Ile|Pro<br>325|Asn|Glu|Leu|Pro|Tyr<br>330|Asn|Asp|Tyr|Phe|Glu<br>335|Tyr|
|Phe|Gly|Pro|Asp<br>340|Phe|Lys|Leu|His|Ile<br>345|Ser|Pro|Ser|Asn|Met<br>350|Thr|Asn|
|Gln|Asn|Thr<br>355|Asn|Glu|Tyr|Leu|Glu<br>360|Lys|Ile|Lys|Gln|Arg<br>365|Leu|Phe|Glu|
|Asn|Leu<br>370|Arg|Met|Leu|Pro|His<br>375|Ala|Pro|Gly|Val|Gln<br>380|Met|Gln|Ala|Ile|
|Pro<br>385|Glu|Asp|Ala|Ile|Pro<br>390|Glu|Glu|Ser|Gly|Asp<br>395|Glu|Asp|Glu|Asp|Asp<br>400|
|Pro|Asp|Lys|Arg|Ile<br>405|Ser|Ile|Cys|Ser|Ser<br>410|Asp|Lys|Arg|Ile|Ala<br>415|Cys|
|Glu|Glu|Glu|Phe<br>420|Ser|Asp|Ser|Glu|Glu<br>425|Gly|Glu|Gly|Gly<br>430|Arg|Lys|
|Asn|Ser|Ser<br>435|Asn|Phe|Lys|Lys|Ala<br>440|Lys|Arg|Val|Lys|Thr<br>445|Glu|Asp|Glu|
|Lys|Glu<br>450|Lys|Asp|Pro|Glu|Glu<br>455|Lys|Lys|Glu|Val|Thr<br>460|Glu|Glu|Glu|Lys|
|Thr<br>465|Lys|Glu|Glu|Lys|Pro<br>470|Glu|Ala|Lys|Gly|Val<br>475|Lys|Glu|Glu|Val|Lys<br>480|
|Leu|Ala<br>482| | | | | | | | | | | | | | |

( 2 ) INFORMATION FOR SEQ ID NO: 2:

( i ) SEQUENCE CHARACTERISTICS:
        ( A ) LENGTH: 2111
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homo sapiens ( v i i ) IMMEDIATE SOURCE:
        ( A ) LIBRARY: human fetal lung cDNA library ( i x ) FEATURE:
        ( A ) NAME/KEY: CDS
        ( B ) LOCATION: 64..1512
        ( C ) IDENTIFICATION METHOD: experimental examination ( x i ) SEQUENCE DESCRIPTION: SEQ ID NO: 2:

```
GAGCGGAGCC  GCGGGCGGGA  GGGCGGACGG  ACCGACTGAC  GGTAGGGACG  GGAGGCGAGC        60
```

| | | | | | | | | | | | | | | | | |
|---|---|---|---|---|---|---|---|---|---|---|---|---|---|---|---|---|
|AAG|ATG|GCG|CAG|ACG|CAG|GGC|ACC|CGG|AGG|AAA|GTC|TGT|TAC|TAC|TAC|108|
| |Met<br>1|Ala|Gln|Thr|Gln<br>5|Gly|Thr|Arg|Arg|Lys<br>10|Val|Cys|Tyr|Tyr|Tyr<br>15| |
|GAC|GGG|GAT|GTT|GGA|AAT|TAC|TAT|TAT|GGA|CAA|GGC|CAC|CCA|ATG|AAG|156|
|Asp|Gly|Asp|Val|Gly<br>20|Asn|Tyr|Tyr|Tyr|Gly<br>25|Gln|Gly|His|Pro|Met<br>30|Lys| |
|CCT|CAC|CGA|ATC|CGC|ATG|ACT|CAT|AAT|TTG|CTG|CTC|AAC|TAT|GGT|CTC|204|
|Pro|His|Arg|Ile<br>35|Arg|Met|Thr|His|Asn<br>40|Leu|Leu|Leu|Asn|Tyr<br>45|Gly|Leu| |
|TAC|CGA|AAA|ATG|GAA|ATC|TAT|CGC|CCT|CAC|AAA|GCC|AAT|GCT|GAG|GAG|252|
|Tyr|Arg|Lys|Met<br>50|Glu|Ile|Tyr|Arg|Pro<br>55|His|Lys|Ala|Asn|Ala<br>60|Glu|Glu| |

| | | | | | | | | | | | | | | | | |
|---|---|---|---|---|---|---|---|---|---|---|---|---|---|---|---|---|
| ATG | ACC | AAG | TAC | CAC | AGC | GAT | GAC | TAC | ATT | AAA | TTC | TTG | CGC | TCC | ATC | 300 |
| Met | Thr | Lys | Tyr | His | Ser | Asp | Asp | Tyr | Ile | Lys | Phe | Leu | Arg | Ser | Ile | |
| | 65 | | | | 70 | | | | | 75 | | | | | | |
| CGT | CCA | GAT | AAC | ATG | TCG | GAG | TAC | AGC | AAG | CAG | ATG | CAG | AGA | TTC | AAC | 348 |
| Arg | Pro | Asp | Asn | Met | Ser | Glu | Tyr | Ser | Lys | Gln | Met | Gln | Arg | Phe | Asn | |
| 80 | | | | 85 | | | | | 90 | | | | | | 95 | |
| GTT | GGT | GAG | GAC | TGT | CCA | GTA | TTC | GAT | GGC | CTG | TTT | GAG | TTC | TGT | CAG | 396 |
| Val | Gly | Glu | Asp | Cys | Pro | Val | Phe | Asp | Gly | Leu | Phe | Glu | Phe | Cys | Gln | |
| | | | | 100 | | | | | 105 | | | | | 110 | | |
| TTG | TCT | ACT | GGT | GGT | TCT | GTG | GCA | AGT | GCT | GTG | AAA | CTT | AAT | AAG | CAG | 444 |
| Leu | Ser | Thr | Gly | Gly | Ser | Val | Ala | Ser | Ala | Val | Lys | Leu | Asn | Lys | Gln | |
| | | | 115 | | | | | 120 | | | | | 125 | | | |
| CAG | ACG | GAC | ATC | GCT | GTG | AAT | TGG | GCT | GGG | GGC | CTG | CAC | CAT | GCA | AAG | 492 |
| Gln | Thr | Asp | Ile | Ala | Val | Asn | Trp | Ala | Gly | Gly | Leu | His | His | Ala | Lys | |
| | | 130 | | | | | 135 | | | | | 140 | | | | |
| AAG | TCC | GAG | GCA | TCT | GGC | TTC | TGT | TAC | GTC | AAT | GAT | ATC | GTC | TTG | GCC | 540 |
| Lys | Ser | Glu | Ala | Ser | Gly | Phe | Cys | Tyr | Val | Asn | Asp | Ile | Val | Leu | Ala | |
| | 145 | | | | | 150 | | | | | 155 | | | | | |
| ATC | CTG | GAA | CTG | CTA | AAG | TAT | CAC | CAG | AGG | GTG | CTG | TAC | ATT | GAC | ATT | 588 |
| Ile | Leu | Glu | Leu | Leu | Lys | Tyr | His | Gln | Arg | Val | Leu | Tyr | Ile | Asp | Ile | |
| 160 | | | | | 165 | | | | | 170 | | | | | 175 | |
| GAT | ATT | CAC | CAT | GGT | GAC | GGC | GTG | GAA | GAG | GCC | TTC | TAC | ACC | ACG | GAC | 636 |
| Asp | Ile | His | His | Gly | Asp | Gly | Val | Glu | Glu | Ala | Phe | Tyr | Thr | Thr | Asp | |
| | | | | 180 | | | | | 185 | | | | | 190 | | |
| CGG | GTC | ATG | ACT | GTG | TCC | TTT | CAT | AAG | TAT | GGA | GAG | TAC | TTC | CCA | GGA | 684 |
| Arg | Val | Met | Thr | Val | Ser | Phe | His | Lys | Tyr | Gly | Glu | Tyr | Phe | Pro | Gly | |
| | | | 195 | | | | | 200 | | | | | 205 | | | |
| ACT | GGG | GAC | CTA | CGG | GAT | ATC | GGG | GCT | GGC | AAA | GGC | AAG | TAT | TAT | GCT | 732 |
| Thr | Gly | Asp | Leu | Arg | Asp | Ile | Gly | Ala | Gly | Lys | Gly | Lys | Tyr | Tyr | Ala | |
| | | 210 | | | | | 215 | | | | | 220 | | | | |
| GTT | AAC | TAC | CCG | CTC | CGA | GAC | GGG | ATT | GAT | GAC | GAG | TCC | TAT | GAG | GCC | 780 |
| Val | Asn | Tyr | Pro | Leu | Arg | Asp | Gly | Ile | Asp | Asp | Glu | Ser | Tyr | Glu | Ala | |
| | 225 | | | | | 230 | | | | | 235 | | | | | |
| ATT | TTC | AAG | CCG | GTC | ATG | TCC | AAA | GTA | ATG | GAG | ATG | TTC | CAG | CCT | AGT | 828 |
| Ile | Phe | Lys | Pro | Val | Met | Ser | Lys | Val | Met | Glu | Met | Phe | Gln | Pro | Ser | |
| 240 | | | | | 245 | | | | | 250 | | | | | 255 | |
| GCG | GTG | GTC | TTA | CAG | TGT | GGC | TCA | GAC | TCC | CTA | TCT | GGG | GAT | CGG | TTA | 876 |
| Ala | Val | Val | Leu | Gln | Cys | Gly | Ser | Asp | Ser | Leu | Ser | Gly | Asp | Arg | Leu | |
| | | | | 260 | | | | | 265 | | | | | 270 | | |
| GGT | TGC | TTC | AAT | CTA | ACT | ATC | AAA | GGA | CAC | GCC | AAG | TGT | GTG | GAA | TTT | 924 |
| Gly | Cys | Phe | Asn | Leu | Thr | Ile | Lys | Gly | His | Ala | Lys | Cys | Val | Glu | Phe | |
| | | | 275 | | | | | 280 | | | | | 285 | | | |
| GTC | AAG | AGC | TTT | AAC | CTG | CCT | ATG | CTG | ATG | CTG | GGA | GGC | GGT | GGT | TAC | 972 |
| Val | Lys | Ser | Phe | Asn | Leu | Pro | Met | Leu | Met | Leu | Gly | Gly | Gly | Gly | Tyr | |
| | | 290 | | | | | 295 | | | | | 300 | | | | |
| ACC | ATT | CGT | AAC | GTT | GCC | CGG | TGC | AGG | ACA | TAT | GAG | ACA | GCT | GTG | GCC | 1020 |
| Thr | Ile | Arg | Asn | Val | Ala | Arg | Cys | Arg | Thr | Tyr | Glu | Thr | Ala | Val | Ala | |
| | 305 | | | | | 310 | | | | | 315 | | | | | |
| CTG | GAT | ACG | GAG | ATC | CCT | AAT | GAG | CTT | CCA | TAC | AAT | GAC | TAC | TTT | GAA | 1068 |
| Leu | Asp | Thr | Glu | Ile | Pro | Asn | Glu | Leu | Pro | Tyr | Asn | Asp | Tyr | Phe | Glu | |
| 320 | | | | | 325 | | | | | 330 | | | | | 335 | |
| TAC | TTT | GGA | CCA | GAT | TTC | AAG | CTC | CAC | ATC | AGT | CCT | TCC | AAT | ATG | ACT | 1116 |
| Tyr | Phe | Gly | Pro | Asp | Phe | Lys | Leu | His | Ile | Ser | Pro | Ser | Asn | Met | Thr | |
| | | | | 340 | | | | | 345 | | | | | 350 | | |
| AAC | CAG | AAC | ACG | AAT | GAG | TAC | CTG | GAG | AAG | ATC | AAA | CAG | CGA | CTG | TTT | 1164 |
| Asn | Gln | Asn | Thr | Asn | Glu | Tyr | Leu | Glu | Lys | Ile | Lys | Gln | Arg | Leu | Phe | |
| | | | 355 | | | | | 360 | | | | | 365 | | | |
| GAG | AAC | CTT | AGA | ATG | CTG | CCG | CAC | GCA | CCT | GGG | GTC | CAA | ATG | CAG | GCG | 1212 |
| Glu | Asn | Leu | Arg | Met | Leu | Pro | His | Ala | Pro | Gly | Val | Gln | Met | Gln | Ala | |
| | | 370 | | | | | 375 | | | | | 380 | | | | |

```
ATT CCT GAG GAC GCC ATC CCT GAG GAG AGT GGC GAT GAG GAC GAA GAC    1260
Ile Pro Glu Asp Ala Ile Pro Glu Glu Ser Gly Asp Glu Asp Glu Asp
    385             390                 395

GAC CCT GAC AAG CGC ATC TCG ATC TGC TCC TCT GAC AAA CGA ATT GCC    1308
Asp Pro Asp Lys Arg Ile Ser Ile Cys Ser Ser Asp Lys Arg Ile Ala
400             405                 410                 415

TGT GAG GAA GAG TTC TCC GAT TCT GAA GAG GAG GGA GAG GGG GGC CGC    1356
Cys Glu Glu Glu Phe Ser Asp Ser Glu Glu Glu Gly Glu Gly Gly Arg
                420                 425                 430

AAG AAC TCT TCC AAC TTC AAA AAA GCC AAG AGA GTC AAA ACA GAG GAT    1404
Lys Asn Ser Ser Asn Phe Lys Lys Ala Lys Arg Val Lys Thr Glu Asp
            435                 440                 445

GAA AAA GAG AAA GAC CCA GAG GAG AAG AAA GAA GTC ACC GAA GAG GAG    1452
Glu Lys Glu Lys Asp Pro Glu Glu Lys Lys Glu Val Thr Glu Glu Glu
        450                 455                 460

AAA ACC AAG GAG GAG AAG CCA GAA GCC AAA GGG GTC AAG GAG GAG GTC    1500
Lys Thr Lys Glu Glu Lys Pro Glu Ala Lys Gly Val Lys Glu Glu Val
    465                 470                 475

AAG TTG GCC TGAATGGACC TCTCCAGCTC TGGCTTCCTG CTGAGTCCCT             1549
Lys Leu Ala
480     482

CACGTTTCTT CCCCAACCCC TCAGATTTTA TATTTCTAT TTCTCTGTGT ATTTATATAA   1609

AAATTTATTA AATATAAATA TCCCCAGGGA CAGAAACCAA GGCCCCGAGC TCAGGGCAGC   1669

TGTGCTGGGT GAGCTCTTCC AGGAGCCACC TTGCCACCCA TTCTTCCCGT TCTTAACTTT   1729

GAACCATAAA GGGTGCCAGG TCTGGGTGAA AGGGATACTT TTATGCAACC ATAAGACAAA   1789

CTCCTGAAAT GCCAAGTGCC TGCTTAGTAG CTTTGGAAAG GTGCCCTTAT TGAACATTCT   1849

AGAAGGGGTG GCTGGGTCTT CAAGGATCTC CTGTTTTTTT CAGGCTCCTA AAGTAACATC   1909

AGCCATTTTT AGATTGGTTC TGTTTTCGTA CCTTCCCACT GGCCTCAAGT GAGCCAAGAA   1969

ACACTGCCTG CCCTCTGTCT GTCTTCTCCT AATTCTGCAG GTGGAGGTTG CTAGTCTAGT   2029

TTCCTTTTTG AGATACTATT TTCATTTTTG TGAGCCTCTT TGTAATAAAA TGGTACATTT   2089

CTAAAAAAAA AAAAAAAAA AA                                            2111
```